(12) United States Patent
Castaldi et al.

(10) Patent No.: US 6,815,549 B2
(45) Date of Patent: Nov. 9, 2004

(54) PROCESS FOR THE PREPARATION OF 4-[1-HYDROXY -4-[4-(HYDROXYDIPHENYLMETHLY)-1-PIPERIDINYL]-BUTYL]-α, α-DIMETHYLBENZENEACETIC ACID

(75) Inventors: Graziano Castaldi, Briona (IT); Giuseppe Barreca, Montecchia (IT); Domenico Magrone, Milan (IT)

(73) Assignee: Dinamite Dipharma S.p.A., Basiliano (IT)

( * ) Notice: Subject to any disclaimer, the term of this patent is extended or adjusted under 35 U.S.C. 154(b) by 0 days.

(21) Appl. No.: 10/145,765

(22) Filed: May 16, 2002

(65) Prior Publication Data

US 2002/0198233 A1 Dec. 26, 2002

(30) Foreign Application Priority Data

May 17, 2001 (IT) .................................. RM2001A0260

(51) Int. Cl.$^7$ ............................................ C07D 211/34
(52) U.S. Cl. ........................................ 546/239; 546/240
(58) Field of Search .................................. 546/239, 240

(56) References Cited

U.S. PATENT DOCUMENTS 6,147,216 A * 11/2000 Krauss et al. ............... 546/239

FOREIGN PATENT DOCUMENTS

| WO | WO 93/21156 | 10/1993 |
| WO | WO 97/22344 | 6/1997 |
| WO | WO 97/23213 | 7/1997 |

OTHER PUBLICATIONS

Meier et al. "Hydration of acetylenic compounds without using mercury" CA 118:212438 (1993).*
Konno et al. "Studies on as–triazine derivatives . . . " CA 102:62198 (1985).*
S. H. Kawai et al., "A Facile Synthesis of an Oxidation Product of Terfenadine", J. Org. Chem. 1994, 59, 2620–2622.
Jon L. Wright et al., "Subtype—Selective N–Methyl–D –aspartate Receptor Antagonists: Synthesis and Biological Evaluation of 1-(Arylakynyl) –4–benzylpiperidines," J. Med. Chem., v. 42, 1999, pp. 2469–2477.
Waël Baidossi et al, Hydration of Alkynes by a PtCl$_4$ –Co Catalyst, J. Org. Chem., v. 62, 1997, pp. 669–672.
Makoto Tokunaga et al., "The First Anti–Markovnikov Hydration of Terminal Alkynes: Formation of Aldehydes Catalyzed by a Ruthenium (II) /Phosphane Mixture," Angew. Chem. Int. Ed., v. 37, 1998, pp. 2867–2869.

* cited by examiner

Primary Examiner—Celia Chang
(74) Attorney, Agent, or Firm—Young & Thompson

(57) ABSTRACT

A process for the preparation of 4-[1-hydroxy-4-[4-(hydroxydiphenylmethyl)-1-piperidinyl]-butyl]-α,α-dimethylbenzeneacetic acid (Fexofenadine) of formula

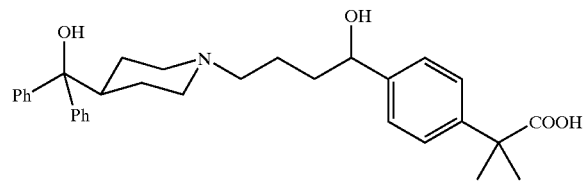

11 Claims, No Drawings

PROCESS FOR THE PREPARATION OF 4-[1-HYDROXY -4-[4-(HYDROXYDIPHENYLMETHLY)-1-PIPERIDINYL]-BUTYL]-α, α-DIMETHYLBENZENEACETIC ACID

The present invention relates to a process for the preparation of 4-[1-hydroxy-4-[4-(hydroxydiphenylmethyl)-1-piperidinyl]-butyl]-alpha,alpha-dimethylbenzeneacetic acid, of formula (7):

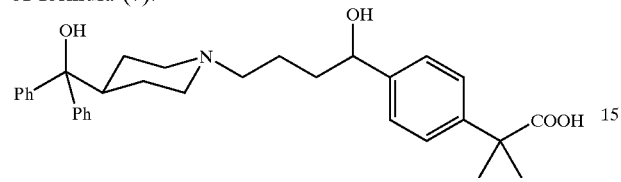

PRIOR ART

A number of processes for the preparation of Fexofenadine (WO93/21156, WO97/22344 WO97/23213) are known. All said processes are characterized by a high number of steps. None of the known processes envisages a convergent approach, on the contrary the final molecule is obtained through the stepwise introduction of the various functions, starting from α,α-dimethylbenzeneacetic acid.

A process is also known (*J. Org. Chem.* 1994, 59, 2620–2622) which is shown in the following scheme 1:

Scheme I

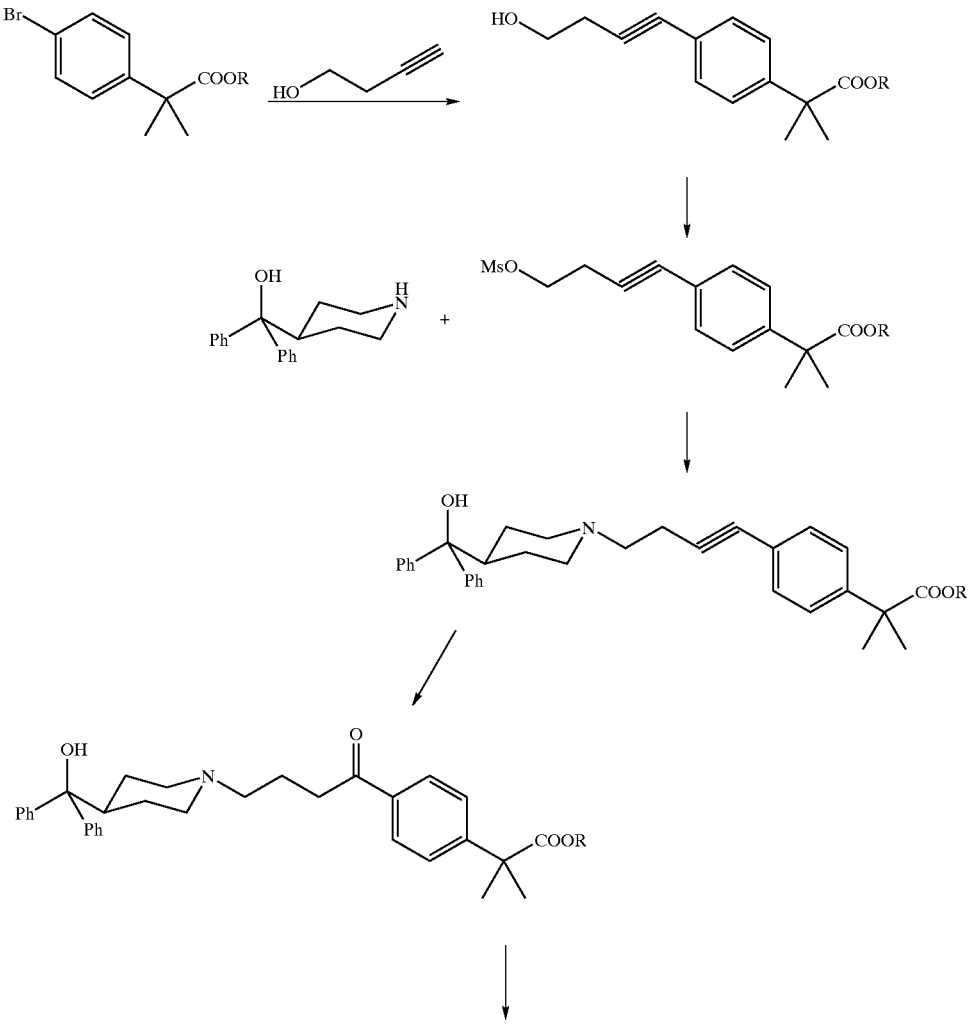

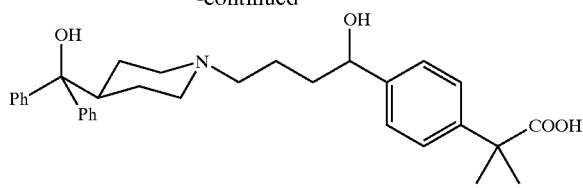

This process suffers from some disadvantages which prevent its industrial application: the oxidation of the triple bond to ketone involves the use of mercuric o mercurous oxide under strongly acidic conditions, which give raise to dehydration by-products, whose formulae are reported in the following, said by-products being difficult to remove from the final product.

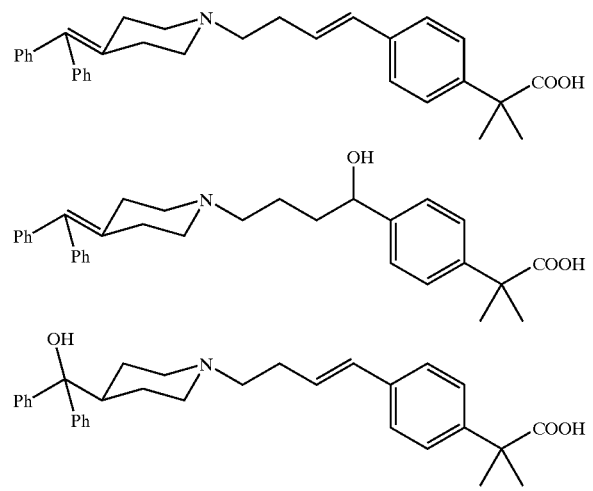

An advantageous process for the preparation of Fexofenadine has now been found, as reported in the following scheme 2:

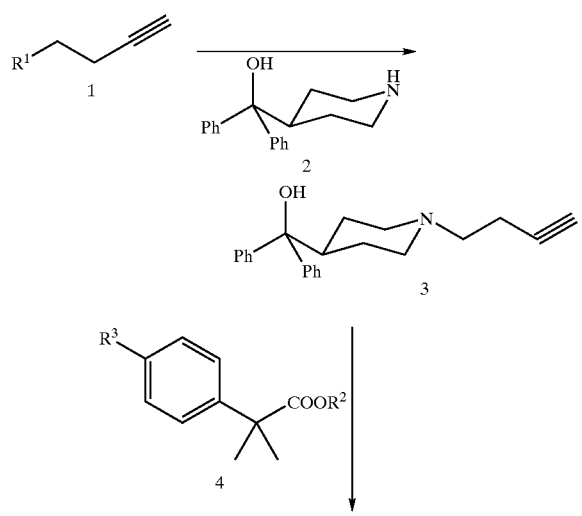

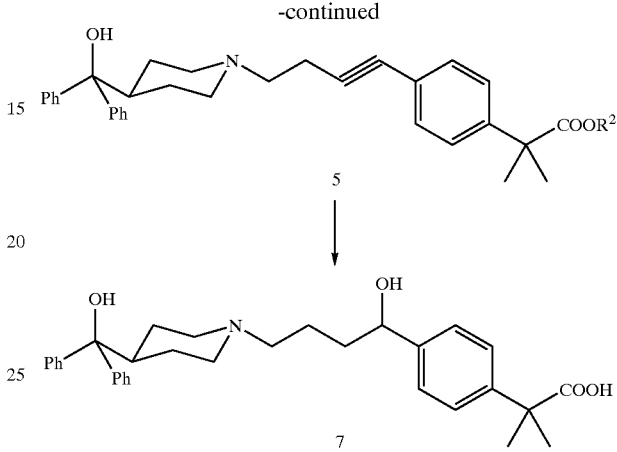

The process of the invention comprises reacting a compound (1) wherein $R^1$ is halogen (chlorine, bromine, iodine) or an alkyl or arylsulfonate group (methanesulfonyl, trifluoromethanesulfonyl, p-toluenesulfonyl and the like) with the compound of formula (2), to give the compound (3).

The reaction is carried out in protic solvents such as water, methanol, ethanol, isopropanol; aprotic dipolar solvents such as acetonitrile, dimethylformamide, dimethylsulfoxide; ethers such as tetrahydrofuran, dibutyl ether, dioxane; esters such as ethyl acetate, butyl acetate; aromatic solvents such as toluene, xylene, benzene; chlorinated solvents such as methylene chloride, chloroform, carbon tetrachloride or mixtures thereof in the presence of an inorganic (carbonates, bicarbonates, alkali or alkaline-earth hydroxides) or organic base (triethylamine, diisopropylethylamine, azacyclonol, and the like) at temperatures ranging from 20° C. to the reflux temperature of the solvent.

Compound (3), which is novel and is a further object of the invention, is then condensed with compound (4) in which $R^2$ is hydrogen o C1–C4 alkyl, and $R^3$ is halogen (chlorine, bromine, iodine) o an alkyl or arylsulfonate (methanesulfonyl, trifluoromethanesulfonyl, p-toluenesulfonyl and the like) in the presence of metal catalysts based on copper(I) or mixtures of palladium(0) and copper(I), in the presence of a base.

The Cu(I) catalyst can consist of copper salts having oxidation state 1, such as cuprous oxide, cuprous chloride, cuprous bromide, cuprous iodide, cuprous acetate, and the like.

The Pd(0) catalyst comprises palladium having oxidation state 0, elemental palladium (metal, cluster, and the like), supported palladium (for example on carbon), palladium complexed with suitable ligands, or palladium generated in situ by reduction of Pd(II) salts, such as palladium acetate, palladium chloride, and the like. Suitable ligands are, for example, phosphorous (III) or nitrogen derivatives. Examples of palladium complexes comprise:

bis-(triphenylphosphine)-dichloro complex bis-(tributylphosphine)-dichloro complex di-allyltriphenylphosphine-dichloro complex tetrakis-(triphenylphosphine) complex triphenylphosphine-piperidine-dichloro complex bis-(triphenylphosphine)-diacetate complex 2,4-pentanedione complex 1,2-bis-(diphenylphosphine)-ethane complex bis-benzonitrile-dichloro complex.

The reaction is preferably carried out in the simultaneous presence of Pd(0), a phosphine ligand and Cu(I) salts, preferably in 1:4:2 Pd:ligand:Cu molar ratios. The palladium molar amount usually ranges from 0.01 to 0.1 relative to compound (3).

Alternatively, the reaction can be carried out in the presence of a Cu(I) salt and of a phosphine ligand in 1:2 Cu:ligand molar ratios. The copper molar amount usually ranges from 0.01 to 0.3 relative to compound (3).

The reaction is optionally carried out in the presence of a solvent selected from water-miscible alcohols, such as methanol, ethanol, isopropanol, 2-methoxy-1-propanol, N,N-dimethylformamide, dimethylsulfoxide, acetonitrile or mixtures thereof with water, in amounts ranging from 1 to 5 volumes relative to compound (3) at a temperature ranging from 20 to 150° C., preferably from 60 to 120° C.

Suitable bases are amino organic bases such as pyridine, piperidine, piperazine, morpholine, diisopropylethylamine, triethylamine, n-octylamine, and the like, preferably triethylamine or inorganic bases such as carbonates, bicarbonates, alkali or alkaline-earth oxides.

A further object of the present invention is the transformation of compound (5) into the corresponding compound (6), which is a precursor of Fexofenadine (7) (scheme 3), with a method which solves the problems described in J. Org. Chem. 1994, 59, 2620 –2622, namely the formation of dehydration products due to the strongly acidic conditions.

The transformation of compound (5) into compound (6) is carried out under neutral conditions in the presence of a catalyst based on palladium(II), platinum(II), ruthenium (III), optionally in the presence of ligands, or in the complexed form. Suitable ligands are phosphorous(III) derivatives, such as triphenylphosphine; nitrogen derivatives, such as benzonitrile, acetonitrile, EDTA or carbonyl derivatives such as carbon oxide, and the like.

The reaction is carried out in the presence of molar amounts of catalyst ranging from 0.005 to 0.1 relative to compound (5), preferably from 0.01 to 0.05.

The reaction is carried out in the presence of a water-miscible solvent, such as methanol, ethanol, isopropanol, tetrahydrofuran, N,N-dimethylformamide, acetonitrile, dimethylsulfoxide in amounts ranging from 1 to 5 volumes relative to compound (5), at a temperature ranging from 20 to 150° C., preferably from 60 to 120° C.

Compound (6) is subsequently transformed into Fexofenadine by hydrolysis of the ester and reduction with sodium borohydride, according to conventional conditions described in literature.

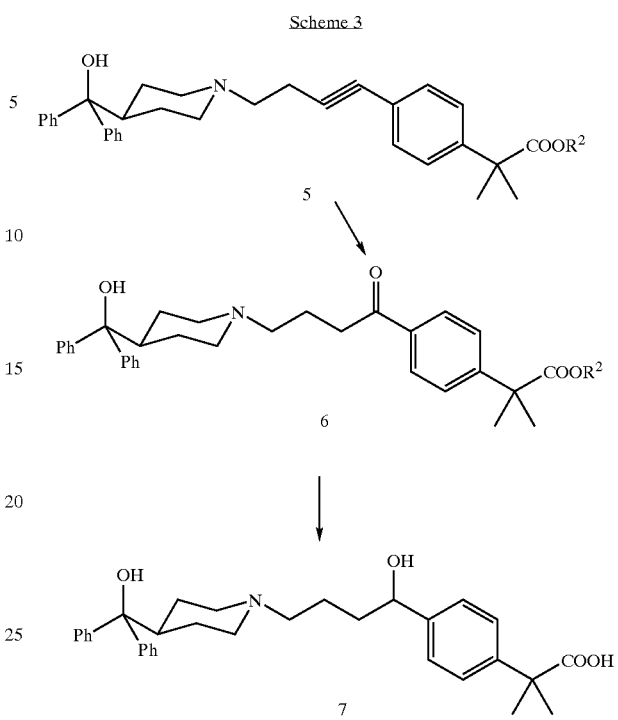

Scheme 3

The following examples illustrate the invention in greater detail.

EXAMPLE 1

Preparation of Compound (1) ($R^1$=OMs)

Methanesulfonyl chloride (57.3 g; 0.5 mols) is dropped under stirring into a solution 3-butyn-1-ol (35 g; 0.5 mols) and triethylamine (55.6 g; 0.55 mols) in methylene chloride (175 ml) keeping the temperature under 30° C. One hour after the addition, water is added (150 ml), the phases are separated, the organic phase is washed with water (100 ml) and concentrated to dryness under vacuum to obtain 1-methanesulfonyl-3-butyn (1) ($R^1$=OMs) as an oily liquid (70.0 g; 94.6% yield).

$^1$H NMR(CDCl$_3$, TMS) δ (ppm): 2.06 (t, 1H); 2.65 (m, 2H); 3.05 (s, 3H); 4.30 (t, 2H).

EXAMPLE 2

Preparation of Compound (3)

Azacyclonol (2) (56.1 g; 0.21 mols) is added to a solution of 1-methanesulfonyl-3-butyn (1) ($R^1$=OMs) (14.8 g; 0.1 mols) in tetrahydrofuran (250 ml). The suspension is refluxed (68° C.) under stirring for 20 hours. The mixture is then cooled to room temperature, filtered, and the azacyclonol methanesulfonate solid is washed with tetrahydrofuran (2×50 ml). The solution is concentrated under vacuum to a residue to yield the desired compound (3) as a viscous liquid (30.5 g; 95.5% yield).

$^1$H NMR(DMSO, TMS) δ (ppm): 1.18 (m, 2H); 1.41 (m, 2H); 1.90 (t, 3H); 2.25 (m, 2H); 2.42 (m, 3H); 2.68 (t, 1H); 2.80 (m, 2H); 7.0–7.6 (aromatics, 10H).

EXAMPLE 3

Preparation of compound (3)

Azacyclonol (2) (56.1 g; 0.21 mols) is added to a solution of 1-bromo-3-butynol (1) ($R^1$=Br) (13.3 g; 0.1 mols) in tetrahydrofuran (250 ml). The suspension is refluxed (68° C.) under stirring for 20 hours. The reaction mixture is cooled to room temperature and filtered, and the solid azacyclonol hydrobromide is washed with tetrahydrofuran (2×50 ml). The solution is concentrated to a residue to yield the desired compound (3) as a viscous liquid (30.7 g; 96.1% yield).

$^1$H NMR(DMSO, TMS) δ (ppm): 1.18 (m, 2H); 1.41 (m, 2H); 1.90 (t, 3H); 2.25 (m, 2H); 2.42 (m, 3H); 2.68 (t, 1H); 2.80 (m, 2H); 7.0 –7.6 (aromatics, 10H).

EXAMPLE 4

Preparation of 4-[(4-hydroxydiphenylmethyl)-1-piperidinyl]-1-butynyl]-α,α-dimethylbenzeneacetic acid methyl ester (5)

Palladium chloride (17.7 mg; 0.1 mmoles), triphenylphosphine (105 mg; 0.4 mmoles) and copper iodide (38 mg; 0.2 mmoles) are added in sequence to a solution of compound (3) (31.9 g; 0.1 mols) and α,α-dimethyl-(4-bromophenyl) acetic acid methyl ester (4) ($R^2$=Me, $R^3$=Br) (25.7 g; 0.1 mols) in triethylamine (120 ml). The mixture is refluxed for 18 hours. The resulting mass is concentrated to a residue under vacuum and diluted with methylene chloride (300 ml) and water (100 ml). The phases are separated and the organic phase is concentrated to a residue, to obtain a solid which is purified by silica gel chromatography (eluent n-heptane:ethyl acetate in 70:30 ratio) to yield the desired compound (5) (40.0 g; 80.7% yield).

$^1$H NMR(DMSO, TMS) δ (ppm): 1.20 (m, 2H); 1.22 (s, 6H); 1.44 (m, 2H); 1.90 (t, 3H); 2.30 (m, 3H); 2.44 (m, 1H); 2.84 (m, 2H); 3.56 (m, 3H); 7.0 –7.9 (aromatics, 14H).

EXAMPLE 5

Preparation of 4-[(4-hydroxydiphenylmethyl)-1-piperidinyl]-1-butynyl]-α,α-dimethylbenzeneacetic acid methyl ester (5)

Palladium chloride (17.7 mg; 0.1 mmoles), triphenylphosphine (105 mg; 0.4 mmoles) and copper iodide (38 mg; 0.2 nmoles) are added in sequence to a solution of (3) (31.9 g; 0.1 mols) and α,α-dimethyl-(4-trifluoromethanesulfonyl) acetic acid methyl ester (4) ($R^2$=Me, $R^3$=$OSO_2CF_3$) (31.0 g; 0.1 mols) in triethylamine (120 ml). The mixture is refluxed for 18 hours. The resulting mass is concentrated to a residue under vacuum and diluted with methylene chloride (300 ml) and water (100 ml). The phases are separated and the organic phase is concentrated to a residue, to obtain a solid which is purified by silica gel chromatography (eluent n-heptane:ethyl acetate 70:30 ratio) to yield the desired compound (5) (35.7 g; 72.0 % yield).

$^1$H NMR(DMSO, TMS) δ (ppm): 1.20 (m, 2H); 1.22 (s, 6H); 1.44 (m, 2H); 1.90 (t, 3H); 2.30 (m, 3H); 2.44 (m, 1H); 2.84 (m, 2H); 3.56 (m, 3H); 7.0 –7.9 (aromatics, 14H).

EXAMPLE 6

Preparation of 4-[(4-hydroxydiphenylmethyl)-1-piperidinyl]-1-butynyl]-α,α-dimethylbenzeneacetic acid methyl ester (5)

Copper iodide (190 mg; 1 mmole), triphenylphosphine (524 mg; 2 mmoles) and potassium carbonate (27.6 g; 0.2 mmoles) are added in sequence to a solution of (3) (31.9 g; 0.1 mols) and α,α-dimethyl-(4-bromophenyl)acetic acid methyl ester (4) ($R^2$=Me, $R^3$=Br) (25.7 g; 0.1 mols) in N,N-dimethylformamide (100 ml). The mixture is refluxed for 10 hours. The resulting mass is concentrated to a residue under vacuum and diluted with methylene chloride (300 ml) and water (100 ml). The phases are separated and the organic phase is concentrated to a residue, to obtain a solid which is purified by silica gel chromatography (eluent n-heptane:ethyl acetate 70:30 ratio) to yield the desired compound (5) (41.1 g; 83% yield).

$^1$H NMR(DMSO, TMS) δ (ppm): 1.20 (m, 2H); 1.22 (s, 6H); 1.44 (m, 2H); 1.90 (t, 3H); 2.30 (m, 3H); 2.44 (m, 1H); 2.84 (m, 2H); 3.56 (m, 3H); 7.0 –7.9 (aromatic, 14H).

EXAMPLE 7

Preparation of 4-[1-oxo-4-[4-hydroxydiphenylmethyl)-1-piperidinyl]butyl]-α,α-dimethylbenzeneacetic acid methyl ester (6)

Platinum(II) chloride (532 mg; 2.0 mmoles) is added to a solution of (5) (49.5 g; 0.1 mols) in tetrahydrofuran (100 ml) and water (10 ml). The mixture is refluxed for 12 hours, then concentrated to a residue under vacuum and diluted with methylene chloride (300 ml) and water (150 ml). The phases are separated and the organic phase is concentrated to a residue, which is purified by silica gel chromatography (eluent methylene chloride:methanol=15:1) to give the desired product 6 (43.6 g; 85% yield).

$^1$H NMR($CDCl_3$, TMS) δ (ppm): 1.40 (m, 4H); 1.58 (s, 6H); 1.96 (m, 4H); 2.38 (t, 3H); 2.96 (m, 4H); 3.64 (s, 3H); 7.1÷8.0 (aromatics, 14H).

EXAMPLE 8

Preparation of Fexofenadine (7)

Sodium hydroxide (2.4 g, 0.06 mols) and sodium borohydride (0.8 g; 0.02 mols) are added to a solution of compound (6) (20.5 g; 0.04 mols) in methanol (100 ml) and water (30 ml). The mixture is heated at 50° C. for 4 hours, then cooled to room temperature and added with acetone (5 ml). After 30 minutes, 36% hydrochloric acid (12.4 g; 0.122 mols) is added. The resulting suspension is heated to 45° C. to complete dissolution, then is slowly cooled to 0° C. The resulting solid is filtered, washed with water (2×30 ml) and dried under vacuum at 60° C., to obtain Fexofenadine hydrochloride (15.5 g; 72% yield).

$^1$H NMR($CD_3OD$, TMS) δ (ppm): 1.52 (s, 6H); 1.78 (m, 8H); 2.90 (m, 5H); 3.48 (d, 2H); 4.62 (t, 1H); 7.1 –7.6 (aromatics, 14H).

What is claimed is:

1. A process for the preparation of Fexofenadine, which comprises:

a) reaction of a compound of formula (1):

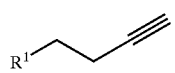

(1)

wherein $R^1$ is a halogen or an alkyl or arylsulfonate group, with the compound of formula (2):

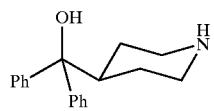

b) condensation of the resulting compound of formula (3):

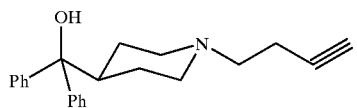

with a compound of formula (4):

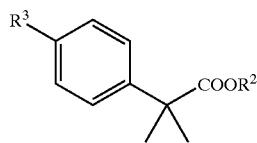

wherein R² is hydrogen or C1–C4 alkyl, and R³ is a halogen or an alkyl or arylsulfonate, in the presence of metal catalysts based on copper(I) or mixtures of palladium(0) and copper(I) in the presence of a base;

c) transformation of the resulting compound of formula (5):

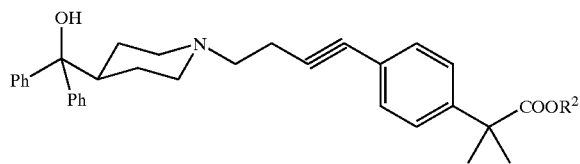

into compound (6):

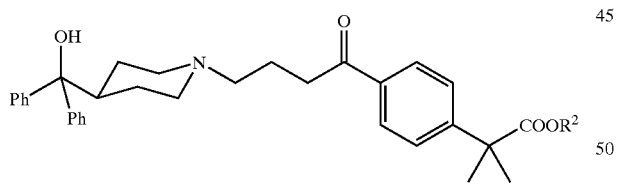

by treatment with water in the presence of a catalyst based on palladium (II), platinum (II), or ruthenium (III), optionally in the presence of ligands.

2. A process as claimed in claim 1, wherein the reaction of step a) is carried out in protic solvents, dipolar aprotic solvents, ethers, esters, aromatic solvents, chlorinated solvents or mixtures thereof in the presence of an inorganic or organic base temperatures ranging from 200° C. to the reflux temperature of the solvent.

3. A process as claimed in claim 1, wherein the Pd(0) catalyst used in step b) comprises palladium having oxidation state 0, elemental palladium, supported palladium, palladium complexed with suitable ligands, or palladium generated in situ by reduction of Pd(II) salts.

4. A process as claimed in claim 1, wherein the Cu(I) catalyst is selected from cuprous oxide, cuprous chloride, cuprous bromide, cuprous iodide, cuprous acetate.

5. A process as claimed in claim 3, wherein the Pd(0) complex is selected from:

bis-(triphenylphosphine)-dichloro complex
bis-(tributylphosphine)-dichloro complex
di-allyltriphenylphosphine-dichloro complex
tetrakis-(triphenylphosphine) complex
triphenylphosphine-piperidine-dichloro complex
bis-(triphenylphosphine)-diacetate complex
2,4-pentanedione complex
1,2-bis-diphenylphosphine)-ethane complex
bis-benzonitrile-dichloro complex.

6. A process as claimed in claim 1, wherein the Pd:ligand:Cu molar ratios are 1:4:2 and the molar amount of palladium used ranges from 0.01 to 0.1 relative to compound (3).

7. A process as claimed in claim 3, wherein the reaction is optionally carried out in the presence of a solvent selected from water-miscible alcohols or mixtures thereof with water, in amounts ranging from 1 to 5 volumes relative to compound (3) at a temperature ranging from 20 to 150° C., preferably from 60 to 120 ° C.

8. A process as claimed in claim 3, wherein the base is selected from pyridine, piperidine, piperazine, morpholine, diisopropylethylamine, triethylamine, n-octylamine.

9. A process as claimed in claim 7, wherein the base is triethylamine.

10. A process as claimed in claim 1, wherein compound (6) is transformed into Fexofenadine (7) by reduction with metal hydrides and hydrolysis of the ester groups.

11. A compound of formula (3):

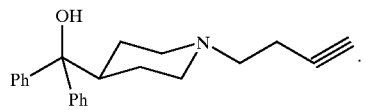

* * * * *